(12) United States Patent
Krsek et al.

(10) Patent No.: US 7,229,557 B2
(45) Date of Patent: Jun. 12, 2007

(54) METHOD TO SEPARATE STEREOISOMERS

(75) Inventors: George R. Krsek, Tucson, AZ (US);
Enrique E. Durazo, Oro Valley, AZ (US)

(73) Assignee: Konec, Inc., Tucson, AZ (US)

( * ) Notice: Subject to any disclaimer, the term of this patent is extended or adjusted under 35 U.S.C. 154(b) by 301 days.

(21) Appl. No.: 10/772,675

(22) Filed: Feb. 4, 2004

(65) Prior Publication Data

US 2005/0171155 A1 Aug. 4, 2005

(51) Int. Cl.
*B01D 15/08* (2006.01)
*A61K 31/445* (2006.01)

(52) U.S. Cl. .................. 210/656; 514/317; 546/192

(58) Field of Classification Search .......... 210/634, 210/635, 638, 639, 656, 806; 514/304, 313, 514/317, 513, 315; 546/225, 227, 233, 238, 546/184, 192; 558/86, 87
See application file for complete search history.

(56) References Cited

U.S. PATENT DOCUMENTS

| 1,920,160 | A | * | 7/1933 | Bruson ..................... 106/222 |
| 2,957,880 | A |   | 10/1960 | Rometsch |
| 3,848,030 | A | * | 11/1974 | Viterbo et al. ............... 558/86 |
| 6,100,401 | A |   | 8/2000 | Prashad et al. |
| 6,121,453 | A | * | 9/2000 | Zavareh .................... 546/238 |
| 6,531,489 | B2 |   | 3/2003 | Harris et al. |

FOREIGN PATENT DOCUMENTS

WO WO 97/27176 7/1997
WO WO 97/32851 9/1997

OTHER PUBLICATIONS

Approaches to the Preparation of Enantiomerically Pure (2R, 2'R)-(+)-threo-Methylphenidate Hydrochloride, Mahavir Prashad, Adv. Synth. Catal. 2001, 343, No. 5, pp. 379-392, Wiley-Vch Verlag GrmbH 694541 Weinhelm, Germany, 2001, downloaded from the Internet Apr. 28, 2006.*
Search for New Drugs, threo AND erythro Isomers of Methyl a-Phenyl-a-(2-Piperidyl)Acetate Hydrochloride, Yakhontov et al, UDC 615.214.31.012.1, published in 1974 by Consultants Bureau, a division of Plenum Publishing Corporation, downloaded from the Internet Apr. 28, 2006.*
"1-Menthoxyacetic Acid", Organic Synthesis, Coll. vol. 3, p. 544, (1955); vol. 23, p. 52 (1943), downloaded from the Internet Apr. 28, 2006.*
Factsheet, DBGET Result COMPOUND C02344, DBGET integrated database retreival system, GenomeNet, downloaded from the internet Apr. 28, 2006.*

* cited by examiner

*Primary Examiner*—Joseph Drodge
(74) *Attorney, Agent, or Firm*—Chandler & Udall LLP; Dale F Regelman

(57) ABSTRACT

A method to resolve the stereoisomers of an optically active compound comprising an amine moiety. The method provides a mixture comprising two stereoisomers of a compound comprising a amine moiety. The method supplies l-fenchyloxyacetic acid, treats the mixture of stereoisomers with that l-fenchyloxyacetic acid, and collects one of those two stereoisomers having greater than a 99 percent enantiomeric excess.

10 Claims, 2 Drawing Sheets

METHOD TO SEPARATE STEREOISOMERS

FIELD OF THE INVENTION

Applicant's invention relates to a method to separate stereoisomers. In certain embodiments, Applicants' invention relates to a method to isolate d-threo-methylphenidate having greater than a 99 percent enantiomeric excess from a mixture of d-threo-methylphenidate and l-threo-methylphenidate.

BACKGROUND OF THE INVENTION

Attention Deficit Disorder (ADD), a commonly diagnosed nervous system illness in children, is often treated with methylphenidate hydrochloride. Methylphenidate is sold in commerce under the name Ritalin®. Ritalin is a registered trademark owned by Novartis Corporation.

Symptoms of ADD include distractibility and impulsivity. A related disorder, termed Attention Deficit Hyperactivity Disorder (ADHD), is further characterized by symptoms of hyperactivity, and is also treated with methylphenidate hydrochloride. Methylphenidate drugs have also been used to treat cognitive decline in patients with Acquired Immunodeficiency Syndrome (AIDS) or AIDS related conditions. See, e.g., Brown, G., Intl. J. Psych. Med. 25(1): 21–37 (1995); Holmes et al., J. Clin. Psychiatry 50:5–8 (1989). These various treatment regimes comprise administering to the patient one or more oral doses of a methylphenidate drug such as methylphenidate hydrochloride.

Methylphenidate exists as four separate optical isomers. These four optical isomers are shown below.

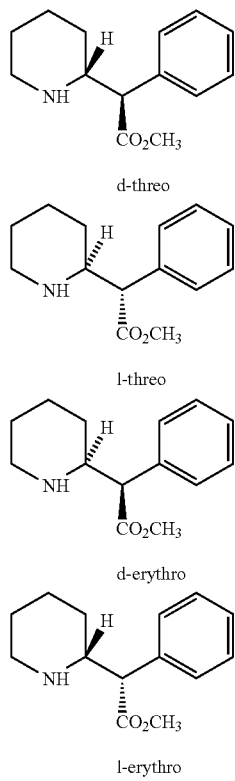

Pharmaceutically acceptable salts of Methylphenidate, the hydrochloride for example, are sometimes administered clinically.

Clinically, the threo pair of enantiomers of methylphenidate hydrochloride is generally administered for the treatment of ADD and ADHD. The hydrochloride salt is commonly referred to simply as "methylphenidate". Unless indicated otherwise, the term "Methylphenidate" is used broadly herein to include methylphenidate and pharmaceutically acceptable salts thereof, including methylphenidate hydrochloride.

The threo racemate (pair of enantiomers) of Methylphenidate is a mild central nervous system stimulant with pharmacological activity qualitatively similar to that of amphetamines. Undesirable side effects associated with the use of the dl-threo racemate of Methylphenidate include anorexia, weight loss, insomnia, dizziness and dysphoria. Furthermore, the racemate, which is a Schedule II controlled substance, produces a euphoric effect when administered intravenously or through inhalation or ingestion, and thus carries a high potential for abuse.

It is known in the art that the pharmacodynamic activity of dl-threo-methylphenidate resides in the d-threo isomer (Clin. Pharmacol. Ther., 52:561–568 (1992)). Therefore, while di-threo-methylphenidate is generally used therapeutically, this racemate includes the l-isomer which apparently makes no significant contribution to the pharmacological effectiveness of the drug, but likely contributes to the associated side effects. It is thus desirable to administer only the active d-threo form of the drug.

SUMMARY OF THE INVENTION

Applicants' invention includes a method to resolve the stereoisomers of an optically active compound comprising an amine moiety. Applicants' method provides a mixture comprising two stereoisomers of a compound comprising a amine moiety. Applicants' method supplies l-fenchyloxyacetic acid, treats the mixture with that l-fenchyloxyacetic acid, and collects one of those two stereoisomers having greater than a 99 percent enantiomeric excess.

In certain embodiments, Applicants' invention includes a method to isolate d-threo-methylphenidate having greater than a 99 percent enantiomeric excess from a mixture of d-threo-methylphenidate and l-threo-methylphenidate. Applicants' method provides a mixture comprising d-threo-methylphenidate and l-threo-methylphenidate. Applicants' method supplies l-fenchyloxyacetic acid, and treats the dl-threo-methylphenidate mixture with that l-fenchyloxyacetic acid. Applicants' method includes collecting d-threo-methylphenidate having greater than a 99 percent enantiomeric excess.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

Applicants' invention is described herein with reference to separating stereoisomers of dl-threo-methylphenidate. This description should not be interpreted as limiting Applicants' invention to separating stereoisomers of methylphenidate, because as a general matter Applicants' invention includes a method to resolve stereoisomers of an optically active compound, where that optically active compound comprises an amine moiety.

References made herein to "methylphenidate," include all four optical isomers of the compound and all pharmaceutically acceptable salts thereof. When one or more particular isomers is contemplated, the isomer is indicated, as in d-threo, l-threo, etc. The combined threo isomers may be indicated simply as "threo," or as dl-threo-methylphenidate As those skilled in the art will appreciate, for therapeutic use in treating conditions treatable by methylphenidate drugs, dl-threo methylphenidate hydrochloride is generally used, while d-threo methylphenidate hydrochloride is preferred.

As discussed, the four isomers have exhibited varying levels of therapeutic activity, and have been shown to differ generally in producing unwanted side effects. The present invention provides a method to obtain d-threo-methylphenidate having greater than a 99 percent enantiomeric excess. Therapeutic use of such d-threo-methylphenidate having greater than a 99 percent enantiomeric excess maximizes therapeutic effectiveness, and minimizes undesirable side effects.

Figure 1:
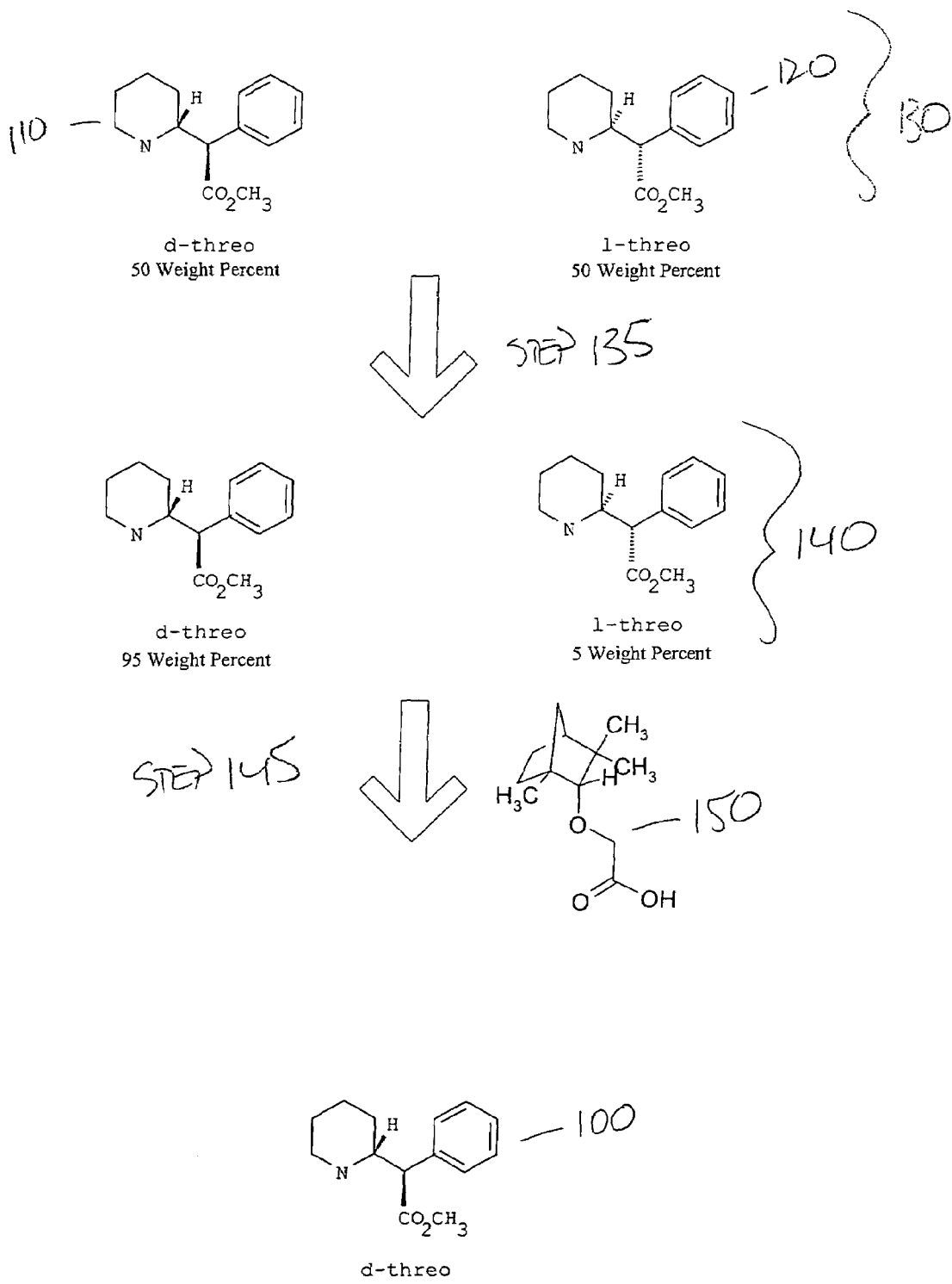
FIG. 1 is a flow chart summarizing Applicants' method.

FIG. 1 summarizes Applicants' method. Mixture 130 comprising dl-threo-methylphenidate includes the desired d-threo-methylphenidate 110 with the less-desired l-threo-methylphenidate 120. In certain embodiments, mixture 130 comprises a racemic mixture of compounds 110 and 120, i.e. a mixture comprising about equal amounts of compounds 110 and 120.

Methylphenidate was first prepared as a mixture of the erythro and threo racemates. U.S. Pat. No. 2,957,880, in the name of Rometsch et al., describes the conversion of certain α-aryl-α-piperidyl-(2)-acetic acids and derivatives thereof, including methylphenidate, into their respective racemates.

Resolution of threo methyphenidate, i.e. separation of compound 110 from mixture 130 is known using, for example, chiral column chromatography, optically active salts, and the like. For example, in step 135 a racemic mixture of compounds 110 and 120 can be separated into a fraction 140 comprising about 95 weight percent d-threo-methylphenidate and about 5 weight percent l-threo-methylphenidate. Such a 95/5 weight percent mixture 140 comprises about a 90 percent enantiomeric excess of the d-threo-methyphenidate stereoisomer. Applicants' method can further enhance that 90 percent enantiomeric excess.

Using one embodiment of Applicants' method, mixture 140 is treated with l-fenchyloxyacetic acid to provide d-threo-methylphenidate having greater than a 99 percent enantiomeric excess, i.e. comprising more than about 99.5 weight percent d-threo-methyphenidate and less than about 0.5 weight percent l-threo-methylphenidate. In certain embodiments, step 145 includes steps 240 (FIG. 2), 245 (FIG. 2), 250 (FIG. 2), and 220 (FIG. 2).

Figure 2:
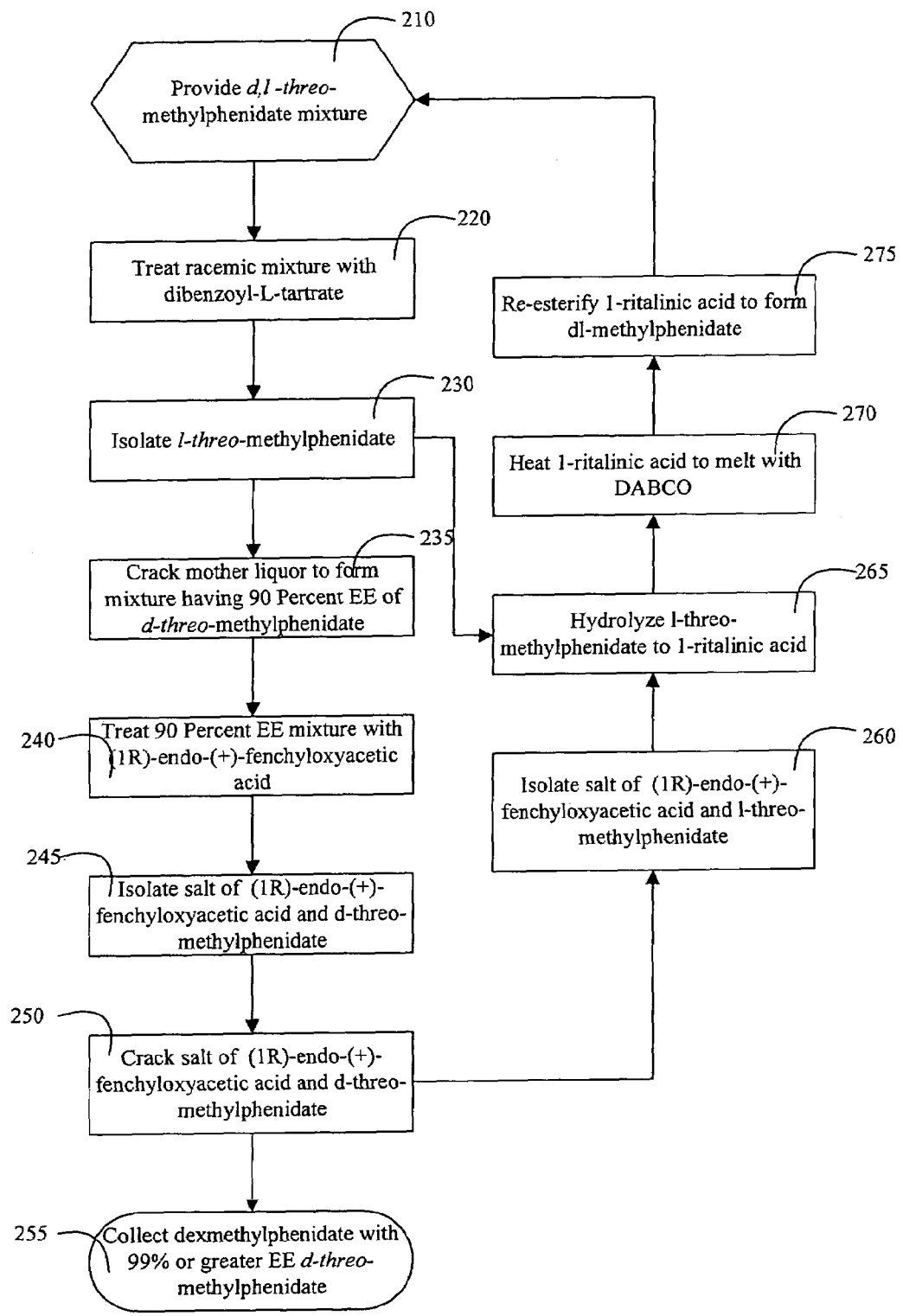
FIG. 2 is a flow chart summarizing the individual steps of Applicants' method.

Referring now to FIG. 2, in step 210 Applicants' method provides a dl-threo-methylphenidate mixture, such as for example mixture 130 (FIG. 1). Applicants' method transitions from step 210 to step 220 wherein the method treats the racemic mixture of step 210 with dibenzoyl-L-tartrate. In step 230, Applicants' method separates most of the l-isomer portion of the mixture of step 210 from a methanolic mother liquor solution containing most of the d-isomer. Example 1 further describes embodiments for steps 225 and 230.

In step 235, Applicants' method "cracks" the mother liquor obtained in step 230. Example 2 further describes one embodiment of step 235. In step 240, Applicants' method treats the d-threo-methylphenidate fraction of step 235 with l-fenchyloxyacetic acid, compound 150. In step 245, Applicants' method isolates the salt of (1R)-endo-(+)-fenchyloxyacetic acid/d-threo-methylphenidate.

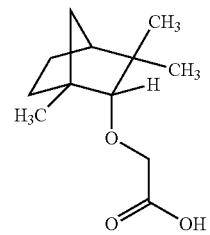

Example 4 recites a synthetic preparation for compound 150. Example 5 describes embodiments for steps 240 and 245.

In step 250, Applicants' method "cracks" the salt of (1R)-endo-(+)-fenchyloxyacetic acid/d-threo-methylphenidate obtained in step 245. Applicants' method transitions from step 250 to step 220 wherein the method collects d-threo-methylphenidate having greater than a 99 percent enantiomeric excess. Example 6 describes embodiments for steps 250 and 220.

The mother liquors from step 250 are used to recover and recycle the unwanted stereoisomer, i.e. the l-threo-methylphenidate, in steps 260, 265, 270, 275, and 210. The l-threo-methylphenidate from step 230 is recycled in steps 265, 270, 275, and 210.

In step 260, the l-threo-methylphenidate is obtained from the mother liquors of step 250. In step 265, Applicants' method hydrolyzes l-threo-methylphenidate to l-ritalinic acid. In step 270, Applicants' method treats the l-ritalinic acid of step 265 with a strong amine. In step 275, l-ritalinic acid is esterified to produce a mixture of dl-threo-methylphenidate. The product of step 275 is provided in step 210, and Applicants' method continues.

EXAMPLES 1 through 10, inclusive, are presented to further illustrate to persons skilled in the art how to make and use Applicants' invention and to identify presently preferred embodiments thereof. These examples are not intended as limitations, however, upon the scope of the invention, which is defined only by the appended claims.

EXAMPLE 1

The l isomer was isolated from the mixture of step 210 by dissolving 31.0 grams of dl-methylphenidate HCl and 41.2 grams of dibenzoyl-L-tartaric acid in 149 mL of methanol at 30 to 30° C. with stirring. To the solution was added 11.6 grams of 4-methylmorpholine at a temperature less than 30° C. The solution was warmed to about 45° C. and 75 mL of water were added over about 10 minutes. The solution was seeded with the l-isomer and allowed to cool with stirring to about 25° C. The resulting slurry was aged overnight at 5° C. The solids were removed by filtration and washed with cold methanol/water (2:1 volume ratio) using two washes of about 15 mL each. The isolated l-isomer was dried on the funnel and then further dried in an air oven at about 55° C. to constant weight. The yield was about 28 grams of an l-isomer/tartaric acid fraction with an enantiomeric excess of about 98 percent for both the l-isomer adduct and for the d-isomer adduct which remained in the mother liquors.

EXAMPLE 2

About 26 grams of the l-isomer/tartaric acid fraction obtained in step 225 were treated with about 85 mL of ethyl acetate and about 4.5 grams of sodium hydroxide in about 85 mL of ice water and stirred for about 15 minutes. The layers were separated and the water layer was back extracted with 2×40 mL of ethyl acetate. The organic layers were combined and washed with about 15 mL of water. The combined water layers were saved for later recovery of the dibenzoyl-L-tartaric acid. The combined ethyl acetate layers were dried, and then the ethyl acetate was removed in vacuo to give about 11.7 grams of l-threo-methylphenidate.

EXAMPLE 3

The methanol/water mother liquors from step 225 were treated with about 300 mL of water to precipitate most of the d-isomer, and those solids were collected and dried. The water fraction was concentrated to in vacuo by removing all of the methanol. The 4-methylmorpholine HCl remained in the water layer and the remaining d-isomer precipitated. The solid d-isomer was collected and dried. The water layer was discarded. The combined d-isomer fraction was treated with a total of about 400 mL of isopropyl acetate and about 70 mL of an aqueous saturated sodium carbonate solution. The ethyl acetate layer was separated and evaporated to dryness in vacuo to give about 13 grams of solids. An assay of those solids showed about 95 percent d-threo-methylphenidate and about 5 percent l-threo-methylphenidate.

EXAMPLE 4

About 200 grams of l-fenchyl alcohol, about 500 mL of dry Toluene, and about 40 grams of metallic sodium were added to a two liter, three neck round bottom flask equipped with a condenser having a first end disposed in one of the necks, a drying tube filled calcium chloride disposed on the second end of that condenser, a mechanical stirrer, and a thermometer.

The reaction mixture was heated until the toluene refluxed gently, with an reaction mixture temperature of about 110° C. As soon as the sodium was melted, stirring was commenced at a rate sufficient to break the molten sodium into a plurality of individual droplets. The reaction mixture was refluxed for an additional 15 hours after which stirring was discontinued and the reaction mixture was allowed to cool to room temperature after which any excess sodium was removed.

This reaction mixture was added to one liter of dry toluene in a three neck, five liter round bottom flask equipped with a dropping funnel, mechanical stirrer and a reflux condenser/drying tube filled with calcium chloride. The five liter flask was heated using an oil bath maintained at about 90° C. About 47.5 grams of monochloroacetic acid in about 400 mL dry toluene were added via the dropping funnel, and the reaction mixture was refluxed for about 48 hours, after which the reaction mixture was allowed to cool to room temperature.

The room temperature reaction mixture was extracted with three 500 mL portions of water. The aqueous layers were combined, and acidified with 20% hydrochloric acid. The l-fenchyloxyacetic acid initially formed a liquid layer onto of the water layer. After standing overnight, the l-fenchyloxyacetic acid solidified and was collected. The crude fenchyloxyacetic acid was washed with water, dried to constant weight in an air oven at a temperature between about 50 to about 55° C., and then recrystallized from isopropyl alcohol, to give about 90 grams of l-fenchyloxyacetic acid.

EXAMPLE 5

About 11.3 grams of crude d-threo-methylphenidate from step 235 and about 12.3 grams of l-fenchyloxyacetic acid, were combined in about 120 mL of methanol, and that mixture was heated to about 45° C. Thereafter, about 60 mL of water were added, and the mixture was cooled to about 25° C. The mixture was aged at 5° C. overnight. Solids were collected by filtration and those solids were washed with a mixture of about 5 mL methanol/5 mL water. The solids were dried in a Buchner funnel, then dried in an air oven at a temperature of about 55° C. to constant weight. The yield was about 13.1 grams.

EXAMPLE 6

About 13.1 grams of (1R)-endo-(+)-fenchyloxyacetic acid/d-threo-methylphenidate salt isolated in step 245 were treated with about 150 mL of ethyl acetate and about 70 mL of about 10% sodium bicarbonate solution to give a pH between 7 and 8. The ethyl acetate layer was separated from the water layer, and the water layer extracted with about 40 mL of ethyl acetate. The combined ethyl acetate portions were washed with about 20 mL of water, treated with about 3.5 mL of about 36% hydrochloric acid at about 10 to about 15° C., aged for one hour at about 10° C. Solids were collected from that combined ethyl acetate fraction by filtration. The filter cake was washed with about 15 mL of ethyl acetate and dried to give about 6 grams of about 100% d-threo-methylphenidate.

EXAMPLE 7

The mother liquors from step 250 were concentrated in vacuo to recover about 6 grams of a mixture of d- and l-isomers.

EXAMPLE 8

About 5.1 grams of l-threo-methylphenidate, from step 260 and/or step 230, were refluxed in 4 mL of water containing 3 grams of potassium hydroxide. The reaction mixture was cooled to 65° C., about 10 mL of water were added, and the pH adjusted to about 6.2 using 20% acetic acid. After aging for about 4 hours, the solids were collected by filtration, and those solids were washed with about 20 mL of water and dried to give about 4.8 grams of l-ritalinic acid.

EXAMPLE 9

A mixture of about 4.8 grams of l-ritalinic acid and about 3.0 grams of 1,4-diazabicyclo[2.2.2] octane ("DABCO") was heated under nitrogen at about 160° C. for about 5 hours, and then cooled to room temperature. The solids were isolated and treated with about 45 mL of water, 1.4 grams of potassium hydroxide, and about 40 mL of toluene. The layers were separated and the water layer taken to dryness to give dl-ritalinic acid having little or no optical activity, i.e. a racemic mixture.

EXAMPLE 10

About 10.9 grams of dl-ritalinic acid in about 40 mL of methanol saturated with hydrogen chloride gas were reacted. The reaction mixture was refluxed for about 4 hours. The hot reaction mixture was then filtered and the filtrate taken to dryness in vacuo to give about 4.9 grams of dl-threo-methylphenidateHCl. In certain embodiments, the dl-threo-methylphenidateHCl obtained in step 275 was recrystallized from methanol prior to use in step 210.

The embodiments of Applicants' method recited in FIGS. 1 and/or 2 may be implemented separately. Moreover, in certain embodiments, individual steps recited in FIGS. 1 and/or 2, may be combined, eliminated, or reordered. For example, in certain embodiments Applicants' method includes steps 210, 220, 240, 245, and 250. In other embodiments, Applicants' method includes steps 210, 220, 240, 245, 250, 260, 265, 270, and 175. In yet other embodiments, Applicants' method includes steps 210, 215, and 220.

While the preferred embodiments of the present invention have been illustrated in detail, it should be apparent that modifications and adaptations to those embodiments may occur to one skilled in the art without departing from the scope of the present invention as set forth in the following claims.

We claim:

1. A method to isolate d-threo-methylphenidate in greater than 99 percent enantiomeric excess from a racemic mixture of d-threo-methylphenidate and l-threo-methylphenidate, comprising the steps of:
   providing a racemic mixture comprising d-threo-methylphenidate and l-threo-methylphenidate;
   treating said racemic mixture with dibenzoyl-L-tartrate to obtain a second mixture of d-threo-methylphenidate and l-threo-methylphenidate from said racemic mixture, wherein said second mixture comprises d-threo-methylphenidate having greater than a 90 percent enantiomeric excess;
   supplying l-fenchyloxyacetic acid;
   treating said second mixture with said l-fenchyloxyacetic acid;
   collecting d-threo-methylphenidate having greater than a 99 percent enantiomeric excess.

2. The method of claim 1, wherein said supplying step further comprises the steps of:
   providing l-fenchyl alcohol;
   providing chloroacetic acid;
   reacting said l-fenchyl alcohol with said chloroacetic acid to form said l-fenchyloxyacetic acid.

3. The method of claim 1, wherein said treating step includes the following steps:
   reacting said second mixture with said l-fenchyloxyacetic acid;
   isolating the salt of (1R)-endo-(+)-fenchyloxyacetic acid and d-threo-methylphenidate; and
   cracking said salt of (1R)-endo-(+)-fenchyloxyacetic acid and d-threo-methylphenidate.

4. The method of claim 3, wherein said cracking step includes the following steps:
   providing a 10 percent solution of sodium bicarbonate in water;
   treating the salt of (1R)-endo-(+)-fenchyloxyacetic acid and d-threo-methylphenidate with said aqueous sodium bicarbonate solution and ethyl acetate to give a two phase mixture comprising a water fraction and an ethyl acetate fraction;
   separating the ethyl acetate fraction from said water fraction; and
   treating said ethyl acetate fraction with hydrochloric acid.

5. The method of claim 4, further comprising the steps of:
   obtaining l-threo-methylphenidate from said water fraction;
   hydrolyzing said l-threo-methylphenidate to l-ritalinic acid;
   reacting said l-ritalinic acid with a methanol solution saturated with hydrogen chloride to form dl-methylphenidate.

6. The method of claim 1, wherein said obtaining step includes the steps of:
   reacting said racemic mixture with dibenzoyl-L-tartrate in methanol to give insoluble solids and a methanolic solution;
   separating said insoluble solids and said methanolic solution;
   adding water to said methanolic solution;
   filtering said water/methanol solution to collect said second mixture.

7. The method of claim 6, wherein said treating step includes:
   reacting said second mixture with said l-fenchyloxyacetic acid;
   isolating the salt of (1R)-endo-(+)-fenchyloxyacetic acid and d-threo-methylphenidate; and
   cracking said salt of (1R)-endo-(+)-fenchyloxyacetic acid and d-threo-methylphenidate.

8. The method of claim 7, wherein said cracking step includes the following steps:
   providing a 10 percent solution of sodium bicarbonate in water;
   treating the salt of (1R)-endo-(+)-fenchyloxyacetic acid and d-threo-methylphenidate with said aqueous sodium bicarbonate solution and ethyl acetate to give a two phase mixture comprising a water fraction and an ethyl acetate fraction;
   separating the ethyl acetate fraction from said water fraction; and treating said ethyl acetate fraction with hydrochloric acid.

9. The method of claim 6, wherein said insoluble solids comprises the adduct of l-threo-methylphenidate and said optically active-acid, further comprising the steps of:
   forming l-ritalinic acid from said insoluble solids;
   providing a saturated solution of hydrogen chloride in methanol;
   esterifying said l-ritalinic acid using said saturated solution to form said racemic mixture.

10. A method to resolve stereoisomers of methylphenidate, comprising the steps of:
    providing a mixture comprising d-threo methylphenidate and l-threo methylphenidate;
    supplying l-fenchyloxyacetic acid;
    treating said mixture with said l-fenchyloxyacetic acid; and
    collecting d-threo methylphenidate having greater than a 99 percent enantiomeric excess.

* * * * *

UNITED STATES PATENT AND TRADEMARK OFFICE
CERTIFICATE OF CORRECTION

PATENT NO. : 7,229,557 B2 Page 1 of 1
APPLICATION NO. : 10/772675
DATED : June 12, 2007
INVENTOR(S) : Krsek et al.

It is certified that error appears in the above-identified patent and that said Letters Patent is hereby corrected as shown below:

Claim 10, Col. 8, lines 58-60, "I-threo" and "I-fenchyloxyacetic" should read --1-threo-- and --1-fenchyloxyacetic--, respectively.

Signed and Sealed this

Twenty-third Day of September, 2008

JON W. DUDAS
*Director of the United States Patent and Trademark Office*